United States Patent
Weiss

(10) Patent No.: US 12,364,409 B2
(45) Date of Patent: Jul. 22, 2025

(54) SYSTEM FOR DETECTION OF RF INDUCED HEATING OF A PATIENT UNDERGOING A MRI EXAMINATION

(71) Applicant: KONINKLIJKE PHILIPS N.V., Eindhoven (NL)

(72) Inventor: Steffen Weiss, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 258 days.

(21) Appl. No.: 17/919,782

(22) PCT Filed: Apr. 26, 2021

(86) PCT No.: PCT/EP2021/060778
§ 371 (c)(1),
(2) Date: Oct. 19, 2022

(87) PCT Pub. No.: WO2021/224038
PCT Pub. Date: Nov. 11, 2021

(65) Prior Publication Data
US 2023/0165479 A1 Jun. 1, 2023

(30) Foreign Application Priority Data
May 8, 2020 (EP) .................... 20173614

(51) Int. Cl.
*G01R 33/48* (2006.01)
*A61B 5/00* (2006.01)
*A61B 5/055* (2006.01)
*G01R 33/3415* (2006.01)
*G01R 33/28* (2006.01)

(52) U.S. Cl.
CPC ............ *A61B 5/055* (2013.01); *A61B 5/0033* (2013.01); *G01R 33/28* (2013.01); *G01R 33/3415* (2013.01); *G01R 33/48* (2013.01)

(58) Field of Classification Search
CPC .. A61B 5/055; A61B 5/0033; G01R 33/4804; G01R 33/3804; G01R 33/288; G01R 33/3685; G01K 11/32; G01K 13/00
See application file for complete search history.

(56) References Cited

U.S. PATENT DOCUMENTS 5,362,478 A 11/1994 Desai et al.
5,916,161 A 6/1999 Ishihara et al.
(Continued)

FOREIGN PATENT DOCUMENTS

DE 10029341 A1 1/2002
WO 2014076603 A1 5/2014
(Continued)

OTHER PUBLICATIONS

Homann et al "Local SAR Management by RF Shimming: a Simulation Study with Multiple Human Body Models" Magn. Reson. Mater. Phys. (2012) 25 p. 193-204.
(Continued)

*Primary Examiner* — Boniface N Nganga

(57) ABSTRACT

The present invention relates to a system (10) for detection of Radio Frequency (RF) induced heating of a patient undergoing a Magnetic Resonance Imaging (MRI) examination. The system comprises a form (20); and a processing unit (30). The form is configured to be placed around at least a part of a patient undergoing a Magnetic Resonance Imaging "MRI" examination in an MRI scanner. The form comprises a material (40), and the form is configured such that the material is in thermal contact with the patient when the form is placed around the at least part of the patient undergoing the MRI examination. The processing unit is configured to receive interrogation data of the material. The processing unit is configured to determine that RF induced (Continued)

heating of the patient has occurred. The determination comprises utilization of the interrogation data.

22 Claims, 1 Drawing Sheet

(56) References Cited

U.S. PATENT DOCUMENTS

| | | | |
|---|---|---|---|
| 11,291,383 B2 | 4/2022 | Watts et al. | |
| 2013/0022548 A1* | 1/2013 | Bennett | G01N 24/08 424/9.3 |
| 2014/0070811 A1* | 3/2014 | Tomiha | G01R 33/36 324/322 |
| 2016/0291103 A1* | 10/2016 | Van Leeuwen | G01K 13/00 |
| 2017/0027449 A1 | 2/2017 | O'Neill | |
| 2017/0269176 A1 | 9/2017 | Weiss | |
| 2018/0117186 A1* | 5/2018 | Camley | A61B 5/055 |
| 2021/0284943 A1 | 9/2021 | Akashi et al. | |

FOREIGN PATENT DOCUMENTS

| | | |
|---|---|---|
| WO | 2015129881 A1 | 9/2015 |
| WO | 2019180464 A1 | 9/2019 |

OTHER PUBLICATIONS

Matsukawa et al "Structural and Dynamic Behavior of Polymer Gels as Elucidated by Nuclear Magnetic Resonance Spectroscopy" Polymer Gels and Networks, 2001 CRC Press p. 234.

Cao et al "Poly(N-isopropylacylamide) Chitosan as Thermosensitive in Situ Gel Forming System for Ocular Drug Delivery" J. of Controlled Release (2007) p. 186-194 vol. 120(3).

Jana Vincent et al "Stitching Stretchable Radiofrequency Coils for MRI: A Conductive Tread and Athletic Fabric Approach" 2019 41st Annual International Conf. on the IEEE Engineering in Medicine and Biology Soc. Jul. 23, 2019 p. 679806891.

https://www.gehealthcare.com/products/magnetic-resonance-imaging/air-technology downloaded Oct. 7, 2022.

Andreas Port et al "Liquid metal in stretchable tubes: A wearable 4-channel knee array" Proceedings ISMRM 2019 #1114.

W. Forrest "Strechable MRI Coils on the Horizon for MSK Imaging" https://www.auntminnie.com/index.aspx?sec=sup&sub=mri&pag=dis&ItemID=125579 2019.

Chenite R, et al. Rheological characteriszation of thermogelling chitosan/glycerol-phosphate solutions. Carbohydrate Polymers 2001;46:39-47.

Kock FVC and Colnago LA. Rapid method for monitoring chitosan coagulation using low-field NMR relaxometry. Carbohydrate Polymers 2016;50:1-4.

International Search Report and Written Opinion from PCT/EP2021/060778 mailed Jul. 2, 2021.

Panambu et al "Designing Temperature and Ph Sensitive NIPAM Based Polymers" https://www.sigmaaldrich.com/materials-science/polymer-science/nipam-polymers.html.

https://www.nktphotonics.com/lios/en/technology/distributed-temperature-sensing/.

\* cited by examiner

SYSTEM FOR DETECTION OF RF INDUCED HEATING OF A PATIENT UNDERGOING A MRI EXAMINATION

CROSS REFERENCE TO RELATED APPLICATIONS

This application is a U.S. national phase application of International Application No. PCT/EP2021/060778 filed Apr. 26, 2021, which claims the benefit of EP Application Serial No. 20173614.7 filed May 8, 2020 and is incorporated herein by reference.

FIELD OF THE INVENTION

The present invention relates to a system for detection of Radio Frequency (RF) induced heating of a patient undergoing a Magnetic Resonance Imaging (MRI) examination, a wearable patient suit or wearable item with surface receive coils; a method for detection of RF induced heating of a patient undergoing a MRI examination, as well as to a computer program element and a computer readable medium.

BACKGROUND OF THE INVENTION

In MRI imaging or examinations the trend towards higher field strength, shorter scan times, and the upcoming trend towards surface transmit coils has increased the risk of local radio frequency radiation induced heating of the patient. This is also termed Specific Absorption rate (SAR) hotspots in superficial tissue. SAR frequently becomes the limitation for even faster image acquisition. SAR management has been introduced to address this, using large safety margins for SAR during MRI imaging/examinations, SAR and temperature simulations, or B1 shimming to keep local SAR below allowable limits—see for example Homann H, Graesslin I, Eggers H, Nehrke K, Vernickel P, Katscher U, Dossel O, Börnert P. Local SAR management by RF shimming: a simulation study with multiple human body models. Magn. Reson. Mater. Phys. (2012) 25 193-204.

In a standard clinical setting staff help to minimize superficial heating of the patient due to MR imaging/high local SAR by proper patient positioning, cable routing, and supervision during scanning. Staff can interpret a response of a patient as a complaint about elevated heating and thus indicate that RF heating or SAR of the patient is occurring. However, sedated, impaired, or non-knowledgeable patients may not feel or report elevated heating, which may cause mild burns or even long term skin damage. This situation is exacerbated with respect to the move towards full autonomy, where staff may not be present to interact with the patient in order to establish that RF induced heating/SAR is occurring.

As discussed above, SAR often represents the limiting factor for faster examinations. Various approaches have been explored to address this problem, but they all have major limitations:

MRI Temperature Mapping

MRI temperature mapping is not suitable for monitoring of superficial RF heating for several purposes. Most importantly, MRI temperature mapping can only measure temperature differences and this difference measurement is susceptible to errors due to even small amounts of voluntary and physiological motion (easily in the order of 5 to 10 degrees for small motion). After any gross motion (e.g. patient has moved his arm a bit), there is no means to acquire a new baseline temperature by MRI, so that MRI temperature mapping alone is insufficient for monitoring. Secondly, repeated MRI temperature mapping leads to a considerable increase in examination times.

The US patent application US2018/0117186 concerns the use of doped ferrite particles as temperature sensors for non-invasive MR-based thermometry.

SAR Simulation

Simulation of SAR and local heating are computationally intense and require additional scans to provide a patient—specific model (including anatomy, electrical properties, and thermal properties). In addition, simulations are associated with large error margins.

Use of Large Safety Margins

The SAR limits for clinical scanning themselves include safety margins because of the imperfections in SAR monitoring, and SAR models of the MR systems also include safety margins for the same reason. Such margins limit exam times more than actually required. A better knowledge of actual temperatures during scanning may allow lowering those margins.

B1-Shimming

Multi-element system body coils and surface transmission coils have been proposed with the aim to increase the degrees of freedom for SAR management via B1 shimming, but such coils are also prone to causing superficial SAR that is not easy to predict per simulation.

There is a need to address these issues.

SUMMARY OF THE INVENTION

It would be advantageous to have improved means of detecting that RF induced heating or SAR of a patient is occurring undergoing an MRI examination. The object of the present invention is solved with the subject matter of the independent claims, wherein further embodiments are incorporated in the dependent claims. It should be noted that the following described aspects and examples of the invention apply also to the system for detection of RF induced heating of a patient undergoing an MRI examination, the wearable patient suit or wearable item with surface receive coils, the method for detection of RF induced heating of a patient undergoing a MRI examination, as well as to a computer program element and a computer readable medium.

In a first aspect, there is provided a system for detection of Radio Frequency (RF) induced heating of a patient undergoing a Magnetic Resonance Imaging (MRI) examination. The system comprises:

a form; and a processing unit.

The form is configured to be placed around at least a part of a patient undergoing a Magnetic Resonance Imaging "MRI" examination in an MRI scanner. The form comprises a material. The form is configured such that the material is in thermal contact with the patient when the form is placed around the at least part of the patient undergoing the MRI examination. The processing unit is configured to receive interrogation data of the material. The processing unit is configured to determine that RF induced heating of the patient has occurred. The determination comprises utilization of the interrogation data.

In this way, the risk of local RF heating of the patient can be minimized.

In an example, at least one property of the material changes with temperature, and the interrogation data can comprise MRI data of the material.

In an example, the material is configured to undergo a temperature dependent phase transition. The processing unit is configured to analyse the MRI data of the material to determine that the material has undergone the temperature dependent phase transition. The processing unit is configured to determine that RF induced heating of the patient has occurred based on the determination that the material has undergone the temperature dependent phase transition.

In an example, the processing unit is configured to analyse the MRI data of the material to determine where in the form the material has undergone the temperature dependent phase transition.

In an example, the material is configured to undergo the temperature dependent phase transition at a phase transition temperature.

In an example, the material is configured to undergo the temperature dependent phase transition due to RF induced heating of the patient caused by the Mill scanner during the MRI examination of the patient.

In an example, the material is configured to perform a sol-gel transition.

In an example, the material comprises Chitosan.

In an example, the material comprises Poly(N-Isopropylacrylamide).

In an example, the material comprises Chitosan and Poly(N-Isopropylacrylamide).

In an example, the system comprises at least one temperature sensor integrated into the material, and the interrogation data can comprise temperature sensor data from the at least one temperature sensor.

In an example, the at last one sensor comprises one or more fibre optic temperature sensors.

In an example, based on a determination that RF induced heating of the patient has occurred, the processing unit is configured to output information useable to do one or more of the following: change a scan sequence of the MRI scanner to a sequence that delivers a reduced specific absorption rate, stop the scan, alert staff.

In an example, the form is a wearable patient suit or a wearable item with surface receive coils.

In a second aspect, there is provided a wearable patient suit or wearable item with surface reöpceive coils. The wearable patient suit or wearable item with surface receive coils is configured to be placed around at least a part of a patient undergoing a Magnetic Resonance Imaging "MRI" examination in an MRI scanner. The wearable patient suit or wearable item with surface receive coils comprises a material. The wearable patient suit or wearable item with surface receive coils is configured such that the material is in thermal contact with the patient when the wearable patient suit or wearable item with surface receive coils is placed around the at least part of the patient undergoing the MRI examination. Interrogation data of the material is useable to determine that RF induced heating of the patient has occurred.

In a third aspect, there is provided a method for detection of Radio Frequency (RF) induced heating of a patient undergoing a Magnetic Resonance Imaging (MRI) examination. The method comprises:

a) placing a form around at least a part of a patient undergoing a Magnetic Resonance Imaging "MRI" examination in an MRI scanner, wherein the form comprises a material, and wherein the form is configured such that the material is in thermal contact with the patient when the form is placed around the at least part of the patient undergoing the MRI examination;

b) receiving by a processing unit interrogation data of the material; and c) determining by the processing unit that RF induced heating of the patient has occurred, and wherein the determining comprises utilization of the interrogation data.

According to another aspect, there is provided a computer program element controlling one or more of the systems as previously described which, if the computer program element is executed by a processing unit, is adapted to perform the method as previously described.

According to another aspect, there is provided a computer readable medium having stored computer element as previously described.

The computer program element can for example be a software program but can also be a FPGA, a PLD or any other appropriate digital means.

Advantageously, the benefits provided by any of the above aspects equally apply to all of the other aspects and vice versa.

The above aspects and examples will become apparent from and be elucidated with reference to the embodiments described hereinafter.

BRIEF DESCRIPTION OF THE DRAWINGS

Exemplary embodiments will be described in the following with reference to the following drawing.

DETAILED DESCRIPTION OF EMBODIMENTS

Figure 1:
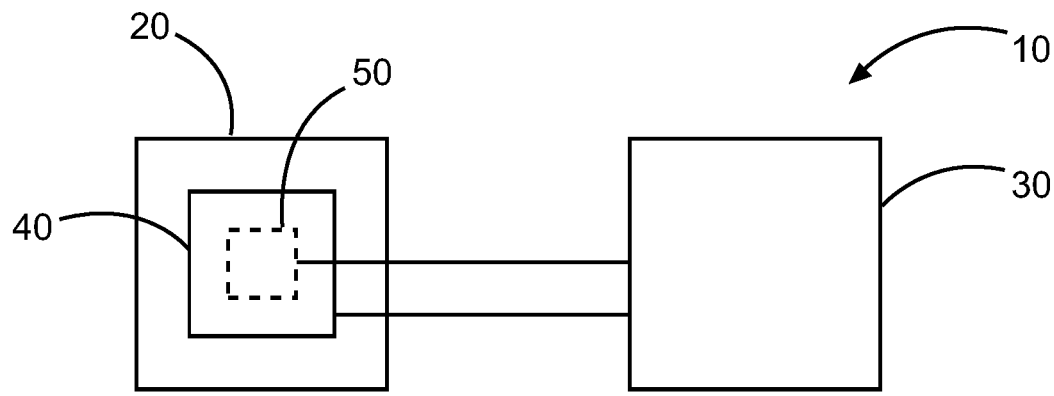
FIG. 1 shows a schematic set up of an example of a system for detection of Radio Frequency induced heating of a patient undergoing a Magnetic Resonance Imaging examination.

FIG. 1 shows a schematic example of a system 10 for detection of Radio Frequency (RF) induced heating of a patient undergoing a Magnetic Resonance Imaging (MRI) examination. The system 10 comprises a form 20, and a processing unit 30. The form is configured to be placed around at least a part of a patient undergoing a Magnetic Resonance Imaging "MRI" examination in an MRI scanner. The form comprises a material 40, and the form is configured such that the material is in thermal contact with the patient when the form is placed around the at least part of the patient undergoing the MRI examination. The processing unit is configured to receive interrogation data of the material. The processing unit is configured to determine that RF induced heating of the patient has occurred. The determination by the processing unit comprises utilization of the interrogation data.

According to an example, at least one property of the material changes with temperature, and the interrogation data can comprise MRI data of the material.

According to an example, the material is configured to undergo a temperature dependent phase transition. The processing unit is configured to analyse the MRI data of the material to determine that the material has undergone the temperature dependent phase transition. The processing unit is configured to determine that RF induced heating of the patient has occurred based on the determination that the material has undergone the temperature dependent phase transition.

According to an example, the processing unit is configured to analyse the MRI data of the material to determine where in the form the material has undergone the temperature dependent phase transition.

According to an example, the material is configured to undergo the temperature dependent phase transition at a phase transition temperature. In an example, the phase transition temperature is in the range of 40° C. to 60° C.

In an example, the phase transition temperature is in the range of 45° C. to 60° C.

In an example, the phase transition temperature is in the range of 40° C. to 50° C.

According to an example, the material is configured to undergo the temperature dependent phase transition due to RF induced heating of the patient caused by the MRI scanner during the MRI examination of the patient.

According to an example, the material is configured to perform a sol-gel transition.

According to an example, the material comprises Chitosan. Alternatively or additionally the material comprises Poly(N-Isopropylacrylamide).

According to an example, the system comprises at least one temperature sensor 50 integrated into the material. The interrogation data can then comprise temperature sensor data from the at least one temperature sensor.

According to an example, the at last one sensor comprises one or more fibre optic temperature sensors.

According to an example, based on a determination that RF induced heating of the patient has occurred, the processing unit is configured to output information useable to do one or more of the following: change a scan sequence of the MRI scanner to a sequence that delivers a reduced specific absorption rate, stop the scan, alert staff.

According to an example, the form is a wearable patient suit or a wearable item with surface receive coils.

From the above description of the system, it is clear that FIG. 1 also relates to a wearable patient suit 20 or wearable item with surface receive coils 20. The wearable patient suit or wearable item with surface receive coils is configured to be placed around at least a part of a patient undergoing a Magnetic Resonance Imaging "MRI" examination in an MRI scanner. The wearable patient suit or wearable item with surface receive coils comprises a material 40. The wearable patient suit or wearable item with surface receive coils is configured such that the material is in thermal contact with the patient when the wearable patient suit or wearable item with surface receive coils is placed around the at least part of the patient undergoing the MRI examination. Interrogation data of the material is useable to determine that RF induced heating of the patient has occurred.

In an example, at least one property of the material changes with temperature. The material is configured such that MRI data of the material is useable as the interrogation data.

In an example, the material is configured to undergo a temperature dependent phase transition.

In an example, the material is configured to undergo the temperature dependent phase transition at a phase transition temperature.

In an example, the phase transition temperature is in the range of 40° C. to 60° C.

In an example, the phase transition temperature is in the range of 45° C. to 60° C.

In an example, the phase transition temperature is in the range of 40° C. to 50° C.

In an example, the material is configured to undergo the temperature dependent phase transition due to RF induced heating of the patient caused by the MRI scanner during the MRI examination of the patient.

In an example, the material is configured to perform a sol-gel transition.

In an example, the material comprises Chitosan.

In an example, the material comprises Poly(N-Isopropylacrylamide).

In an example, at least one temperature sensor 50 is integrated into the material. The temperature sensor data from the at least one temperature sensor is useable as the interrogation data.

In an example, the at last one sensor comprises one or more fibre optic temperature sensors.

Figure 2:
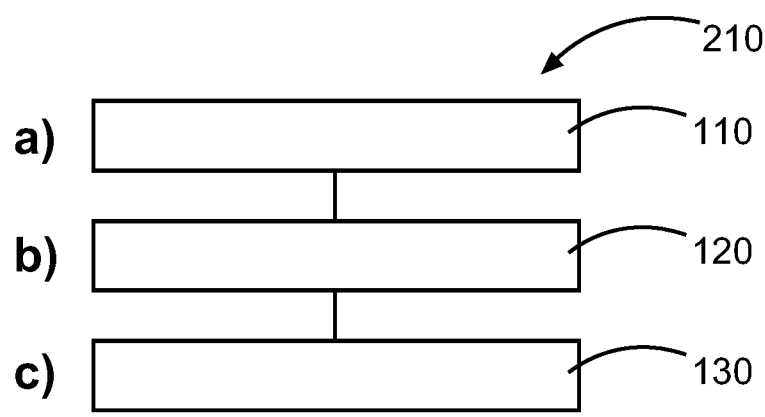
FIG. 2 shows a method for detection of Radio Frequency induced heating of a patient undergoing a Magnetic Resonance Imaging examination.

FIG. 2 shows an example of a method 100 for detection of Radio Frequency (RF) induced heating of a patient undergoing a Magnetic Resonance Imaging (MRI) examination in its basic steps. The method 100 comprises:

in a placing step 110, also referred to as step a), placing a form around at least a part of a patient undergoing a Magnetic Resonance Imaging "MRI" examination in an MRI scanner, wherein the form comprises a material, and wherein the form is configured such that the material is in thermal contact with the patient when the form is placed around the at least part of the patient undergoing the MRI examination;

in a receiving step 120, also referred to as step b), receiving by a processing unit interrogation data of the material; and in a determining step 130, also referred to as step c), determining by the processing unit that RF induced heating of the patient has occurred, and wherein the determining comprises utilization of the interrogation data.

In an example, at least one property of the material changes with temperature, and the interrogation data can comprise MRI data of the material.

In an example, the material is configured to undergo a temperature dependent phase transition. The method then comprises analysing by the processing unit the MRI data of the material to determine that the material has undergone the temperature dependent phase transition. In step c) the determining that RF induced heating of the patient has occurred is based on the determination that the material has undergone the temperature dependent phase transition.

In an example, step c) comprises analyzing by the processing unit the MRI data of the material to determine where in the form the material has undergone the temperature dependent phase transition.

In an example, the material is configured to undergo the temperature dependent phase transition at a phase transition temperature.

In an example, the phase transition temperature is in the range of 40° C. to 60° C.

In an example, the phase transition temperature is in the range of 45° C. to 60° C.

In an example, the phase transition temperature is in the range of 40° C. to 50° C.

In an example, the material is configured to undergo the temperature dependent phase transition due to RF induced heating of the patient caused by the MRI scanner during the MRI examination of the patient.

In an example, the material is configured to perform a sol-gel transition.

In an example, the material comprises Chitosan.

In an example, the material comprises Poly(N-Isopropylacrylamide).

In an example, at least one temperature sensor is integrated into the material, and the interrogation data can comprises temperature sensor data from the at least one temperature sensor.

In an example, the at last one sensor comprises one or more fibre optic temperature sensors.

In an example, based on a determination that RF induced heating of the patient has occurred, the method comprises outputting by processing unit information useable to do one or more of the following: change a scan sequence of the MRI scanner to a sequence that delivers a reduced specific absorption rate, stop the scan, alert staff.

In an example, the form is a wearable patient suit or a wearable item with surface receive coils.

Figure 3:
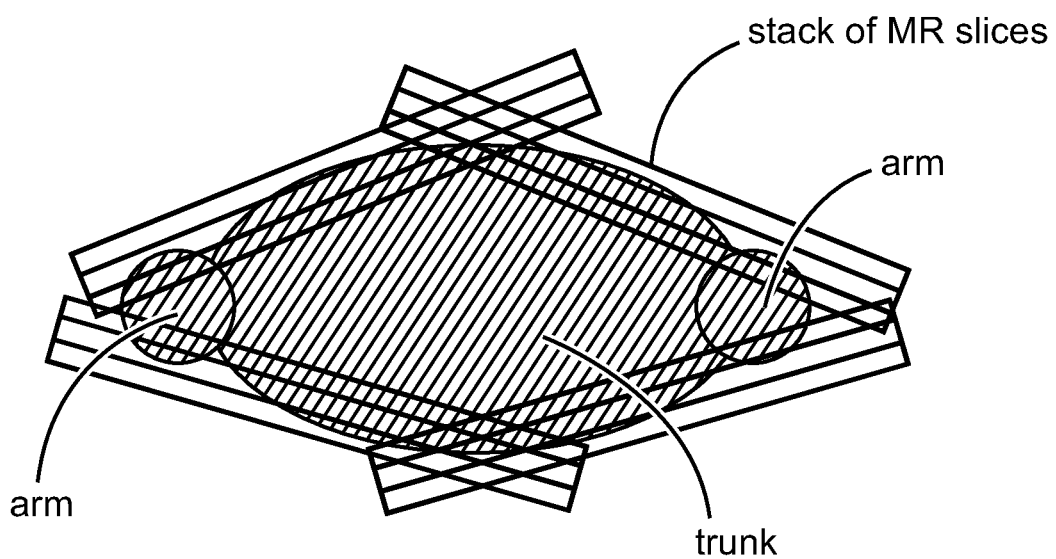
FIG. 3 shows a schematic example of diagnostic MRI data used as interrogation data to of a phase transition material within a wearable suit or within a suit having surface receive coils that is around the patient.

The system for detection of RF induced heating of a patient undergoing a MRI examination, the wearable patient suit or wearable item with surface receive coils, the method for detection of RF induced heating of a patient undergoing a MRI examination are now described in further detail with respect to specific embodiments, where reference is made to FIG. 3.

Standard MRI surface coils are relatively bulky and therefore uncomfortable for the patient. They are also not flexible enough to adapt to the shape of the patient. However, recently, highly flexible and stretchable light-weight receive coils have been developed that fully adapt to the skin of the patient—see for example: https://www.gehealthcare.com/products/magnetic-resonance-imaging/air-technology; https://www.auntminnie.com/index.aspx?sec=sup&sub=mri&pag=dis&ItemID=125579; and Andreas Port, Loris Albisetti, Matij a Varga, Josip Marjanovic, Jonas Reber, David Brunner, Klaas Pruessmann. "Liquid metal in stretchable tubes: A wearable 4-channel knee array". Proceedings ISMRM 2019 #1114.

It was realised by the inventors that patient suits that integrate such wearable coils and cover large parts of the patient could be utilized in a new way. The new technique was that the risk of local RF heating in an autonomous setting could be minimized by superficial temperature measurements performed by the MRI system itself. This is achieved by the integration of a temperature-sensitive material into such wearable forms of light-weight surface receive coils. The material used changes its MRI signal level with temperature due to a phase transition, where the material is in thermal contact with the patient and the temperature change of the material is due to a temperature change of the patient. A patient suit that covers the patient, and that has no surface receive coils, but just has the temperature sensitive material can also be utilized. This approach avoids the difficulties of MRI temperature mapping and works without any additional system components except for the material layer in the wearable coil or patient suit. The approach provides an effective way to determine if RF heating (or SAR) of the patient has occurred and does so in a manner that provides patient comfort.

Wearable coils or even patient suits with such coils, having a temperature sensitive material, in principle offer the opportunity to measure the surface temperature in a global way covering large areas. This efficiently and effectively enables monitoring of RF heating because the locations where heating occurs are not easy to predict. In order that the system for large-area temperature monitoring is compatible with MRI, the first of the following two embodiment achieves this by using the MRI scanner itself for the temperature measurement. This also has cost advantages, because specific temperature sensors are not then required.

In this embodiment, a wearable coil is utilized with a phase-transition material. Many materials undergo phase transitions induced by changes of temperature, and in many cases the phase transition largely changes the MRI signal properties (T1 and T2 relaxation time). Thus, the wearable MRI coil/patient suit is equipped with an inner layer of such material so that it is separated from the skin of the patient only by a thin layer of garment, providing a close thermal contact, when the wearable MRI coil/patient suit is being worn by the patient who is undergoing an MRI examination. The material is chosen to have a phase transition at 40° C. to 60° C., at 45° C. to 60° C., and at 40° C. to 50° C. for example, which changes its MR properties. The material can be configured to have different temperature ranges over which the phase transition occurs, as required. MRI imaging is used to monitor the phase state of the material. This can be done using the MRI scans that are part of the diagnostic exam or by extra scans that are interleaved with diagnostic scanning. Diagnostic 3D scans are suitable because they already include large areas of the skin of the patient.

FIG. 3 shows an example of a patient wearing the wearable MRI coil/patient suit that has the inner layer of the phase transition material. The wearable MRI coil/patient suit is not actually shown. As the patient undergoes the MRI examination, because the phase transition material is in thermal contact with the outside of the patient, for example their skin, if a part of the patient starts to become heated due to SAR, the phase transition material in contact with that part of the patient also heats up, and if the temperature rise is great enough the material will undergo a phase transition, that can be detected from the MRI data.

In FIG. 3 as discussed above the wearable MRI coil/patient suit is not actually shown, but in the locality of the wearable MRI coil/patient suit there are shown extra scans that consist of several stacks of 1-3 slices that cover the surface of the patient, where the wearable MRI coil/patient suit is located. Thus, there are monitoring stacks with few slices each, covering the outer perimeter of the patient. Each stack can be positioned automatically based on the coil sensitivity scan and the survey scan that are performed at the beginning of each MRI examination. The scan time for these extra scans is not prohibitive for several reasons: the signal to noise ratio (SNR) is high because they are positioned adjacent to the receive coil elements, and less than 20 slices are required to cover a large area of the patient.

The scans are repeated at regular intervals, and any large signal change indicating RF heating is used to trigger pre-defined actions as defined below.

Ideal phase transition materials exhibit the following properties:
Provides 1H-MR signal
phase transition at the desired temperature
considerable change of MRI relaxation times due to the phase transition
flexible in both involved phases
allowed as a material7substance in an MRI environment It has been found that Materials that perform a sol-gel transition are suitable for this purpose. A good example is the use of a thermos-gelling aqueous chitosan solution.

Chitosan is an amino-poly-saccharide that can be obtained from chitin, a cellulose-like polymer present e.g. in the exoskeleton of insects. Chitosan is biodegradable and emerging to play a significant role in biomedical applications and food industry—see Chenite R, et al. Rheological characterization of thermogelling chitosan/glycerol-phosphate solutions. Carbohydrate Polymers (2001) 46 39-47.

An aqueous chitosan/glycerol-phosphate solution shows a sol-gel transition at a suitable temperature range around 40 to 50° C., and the temperature of the sol-gel transition can be tuned by choice of the pH value in a biocompatible range around pH=7. The T2 relaxation time of the solution changes from about 2.5s to 1.2s during such a phase transition—see Kock FVC and Colnago LA. Rapid method for monitoring chitosan coagulation using low-field NMR relaxometry. Carbohydrate Polymers (2016) 50 1-4. This results in considerable change of MR signal for turbo-spin-echo (TSE) MR imaging.

A second suitable material system is Poly(N-Isopropylacrylamide) (PNIPAM) in aqueous solution, which undergoes a sol-gel phase transition at around 32° C.—see Matsukawa S et al. Structural and Dynamic Behavior of Polymer Gels as Elucidated by Nuclear Magnetic Resonance Spectroscopy. In: Polymer Gels and Networks. 2001. CRC press. p 234. ISBN-13: 978-0824706692. However, by choice of weight-concentration, coloymerisation with suitable monomers and additives the transition temperature can be tuned—see Cao Y et al. Poly(N-isopropylacrylamide)-chitosan as thermosensitive in situ gel-forming system for ocular drug delivery. J of controlled release (2007) 120(3) 186-194 and https://www.sigmaaldrich.com/materials-science/polymer-science/nipam-polymers.html. It is to be noted that this material is biodegradable and has been used for drug delivery in humans.

Rather than use a phase transition material, a material of the wearable MRI coil/patient suit that is in thermal contact with the patient undergoing the MRI examination has fiber-optic distributed temperature sensors, because they are MRI-safe, i.e. work without any interaction with the MRI system and provide the temperature profile along fibers of several meters length at a time resolution of 1 Hz and higher—see https://www.nktphotonics.com/lios/en/technology/distributed-temperature-sensing/.

A fiber, that can be several metres in length, is embedded in meander loops in the material of the wearable MR surface coil. If any temperature increase along the fiber is detected, the known meander shape of the fiber can be used to determine the location of the hot spot on the patient.

The temperature data in the above embodiments is used to automatically trigger actions such as:
  change of the sequence into a mode that delivers less SAR (in W/Kg) stopping the scan in case of excessive heating
  alerting staff to handle the situation In another exemplary embodiment, a computer program or computer program element is provided that is characterized by being configured to execute the method steps of the method according to one of the preceding embodiments, on an appropriate apparatus or system.

The computer program element might therefore be stored on a computer unit, which might also be part of an embodiment. This computing unit may be configured to perform or induce performing of the steps of the method described above. Moreover, it may be configured to operate the components of the above described apparatus and/or system. The computing unit can be configured to operate automatically and/or to execute the orders of a user. A computer program may be loaded into a working memory of a data processor. The data processor may thus be equipped to carry out the method according to one of the preceding embodiments.

This exemplary embodiment of the invention covers both, a computer program that right from the beginning uses the invention and computer program that by means of an update turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, USB stick or the like, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A system for detection of radio frequency (RF) induced heating of a patient undergoing a magnetic resonance imaging (MRI) examination, the system comprising:
   a form; and
   a processing unit;
   wherein, the form is configured to be placed around at least a part of a patient undergoing a MRI examination in an MRI scanner;
   wherein, the form comprises a material, and wherein the form is configured such that the material is in thermal contact with the patient when the form is placed around the at least part of the patient undergoing the MRI examination;
   wherein, the processing unit is configured to receive interrogation data of the material; and
   wherein, the processing unit is configured to determine that RF induced heating of the patient has occurred, and wherein the determination comprises utilization of the interrogation data, wherein at least one property of the material changes with temperature, and wherein the interrogation data comprises MRI data of the material and wherein the material is configured to undergo a temperature dependent phase transition, and wherein the processing unit is configured to analyse the MRI data of the material to determine that the material has undergone the temperature dependent phase transition, and wherein the processing unit is configured to determine that RF induced heating of the patient has occurred based on the determination that the material has undergone the temperature dependent phase transition.

2. The system of claim 1, wherein the processing unit is configured to analyse the MRI data of the material to determine where in the form the material has undergone the temperature dependent phase transition.

3. The system of claim 1, wherein the material is configured to undergo the temperature dependent phase transition at a phase transition temperature.

4. The system of claim 2, wherein the material is configured to undergo the temperature dependent phase transition due to RF induced heating of the patient caused by the MRI scanner during the MRI examination of the patient.

5. The system of claim 1, wherein said temperature dependent phase transition is a sol-gel transition.

6. The system of claim 1, wherein the material comprises at least one of Chitosan; or Poly(N-Isopropylacrylamide).

7. The system claim 1, wherein the system comprises at least one temperature sensor integrated into the material, and wherein the interrogation data comprises temperature sensor data from the at least one temperature sensor.

8. The system of claim 7, wherein the at last one sensor comprises one or more fibre optic temperature sensors.

9. The system of claim 7, wherein the at least one temperature sensor is integrated into the material in a meander pattern for determining over a large surface area a location where RF induced heating of the patient has occurred.

10. The system of claim 1, wherein based on a determination that RF induced heating of the patient has occurred, the processing unit is configured to output information useable to do one or more of the following: change a scan sequence of the MRI scanner to a sequence that delivers a reduced specific absorption rate, stop the scan, or alert staff.

11. The system of claim 1, wherein the form is a wearable patient suit or a wearable item with surface receive coils.

12. The system of claim 1, wherein the material is configured to undergo the temperature dependent phase transition at a phase transition temperature, and wherein the temperature dependent phase transition is a change in physical state of matter.

13. The system of claim 12, wherein the change in physical state of matter is a change from a solid-like gel physical state to a liquid-like sol physical state.

14. A wearable patient suit or wearable item with surface receive coils, wherein the wearable patient suit or wearable item with surface receive coils is configured to be placed around at least a part of a patient undergoing a magnetic resonance (MR) imaging (MRI) examination in an MRI scanner; wherein the wearable patient suit or wearable item with surface receive coils comprises a material, and wherein the wearable patient suit or wearable item with surface receive coils is configured such that the material is in thermal contact with the patient when the wearable patient suit or wearable item with surface receive coils is placed around the at least part of the patient undergoing the MRI examination; and wherein interrogation data in form of MR data acquired during the MRI examination of the material is useable determine that the material has undergone the temperature dependent phase transition and to determine that RF induced heating of the patient has occurred from the determination that the phase transition occurred.

15. A method for detection of radio frequency (RF) induced heating of a patient undergoing a magnetic resonance imaging (MRI) examination, the method comprising:
   a) placing a form around at least a part of a patient undergoing an MRI examination in an MRI scanner, wherein the form comprises a material, and wherein the form is configured such that the material is in thermal contact with the patient when the form is placed around the at least part of the patient undergoing the MRI examination;
   b) receiving by a processing unit interrogation data that comprises MRI data of the material and acquired during the MRI examination; and
   c) determining by the processing unit that RF induced heating of the patient has occurred, and wherein the determining comprises utilization of the interrogation data wherein at least one property of the material changes with temperature and the material is configured to undergo a temperature dependent phase transition, and
   d) analysing the MRI data of the material to determine that the material has undergone the temperature dependent phase transition.

16. A computer program element for controlling a magnetic resonance imaging (MRI) system, the computer program element comprising executable instructions stored on a non-transitory computer readable media, such that when executed by a processor of said system is configured to carry out the method of claim 12.

17. The method of claim 15, wherein the processing unit is configured to analyse the MRI data of the material to determine where in the form the material has undergone the temperature dependent phase transition as a result of the thermal contact with the patient.

18. The method of claim 15, wherein the material is configured to undergo the temperature dependent phase transition at a phase transition temperature, and wherein the temperature dependent phase transition is a change in physical state of matter.

19. The method of claim 17, wherein the material is configured to undergo the temperature dependent phase transition due to RF induced heating of the patient caused by the MRI scanner during the MRI examination of the patient.

20. The method of claim 15, wherein said temperature dependent phase transition is a sol-gel transition.

21. The method of claim 15, wherein the material has undergone the temperature dependent phase transition because of direct thermal contact with skin of the patient, and the temperature dependent phase transition indicates, based on the direct thermal contact with skin of the patient, that the skin temperature is indicative of RF induced heating of the patient.

22. The method of claim 15, wherein the material is in thermal contact with a large area of the patient and is temperature sensitive such that analysing the MRI data of the material determines whether any material location in the large area, including all patient areas under examination which may be subject to RF induced heating, has undergone the temperature dependent phase transition due to RF induced heating of the patient.

* * * * *